US005112946A

United States Patent [19]
Maione

[11] Patent Number: 5,112,946
[45] Date of Patent: May 12, 1992

[54] MODIFIED PF4 COMPOSITIONS AND METHODS OF USE

[75] Inventor: Theodore Maione, Wakefield, Mass.

[73] Assignee: Repligen Corporation, Cambridge, Mass.

[21] Appl. No.: 376,333

[22] Filed: Jul. 6, 1989

[51] Int. Cl.$^5$ .................. A61K 7/02; A61K 37/36; C07K 7/00; C07K 7/08
[52] U.S. Cl. .................. 530/324; 530/327; 530/380
[58] Field of Search .................. 530/324, 327, 380; 514/12.15

[56] References Cited

U.S. PATENT DOCUMENTS 4,645,828  2/1987  Twardizik et al.
4,737,580  4/1988  Twardzik et al.

OTHER PUBLICATIONS

R. L. Lundblad and C. M. Noyes, Chemical Reagents for Protein Modification, vol. II, CRC Press (1984) pp. 123-139.
A. White and P. Handler and E. L. Smith, Principles of Biochemistry 5th Edition, McGraw Hill, New York (1973) pp. 804-805, 261.
Folkman, J., S. Taylor, C. Spillberg (1983) "The Role of Heparin in Angiogenesis," Ciba Found. Symp. 100:132-149.
Folkman, J., and M. Klagsbrun (1987) "Angiogenic factors," Science 235:442-447.
Folkman, J. (1984) Angiogenesis: Initiation and Modulation. In *Cancer Invasion and Metastasis: Biologic and Therapeutic Aspects*. G. L. Nicolson and L. Milas, eds. Raven Press, New York, pp. 201-208.
Taylor, S. and J. Folkman (1982) "Protamine is an inhibitor of angiogenesis," Nature 279:307-312.
Duel, T. F., P. S. Keim, M. Farmer, and R. L. Heinrikson (1977) "Amino acid sequence of human platelet factor 4," proc. Natl. Acad. Sci. U.S.A. 74(6):2256-2258.
Duel, T. F., R. M. Senior, D. Chang, G. L. Griffin, R. L. Heinrikson, and E. T. Kaiser (1981) "Platelet factor 4 is chemotactic for neutrophils and monocytes," Proc. Natl. Acad. Sci. U.S.A. 78:4585-4587.
Osterman, D. G., G. L. Griffin, R. M. Senior, E. T. Kaiser, and T. F. Deuel (1982) "The carboxyl-terminal tridecapeptide of platelet factor 4 is a potent chemotactic agent for monocytes," Biochem. and Biophys. Res. Comm. 107(1):130-135.

*Primary Examiner*—Margaret Moskowitz
*Assistant Examiner*—Shelly J. Guest
*Attorney, Agent, or Firm*—Saliwanchik & Saliwanchik

[57] ABSTRACT

The subject invention pertains to the use of modified PF4 and recombinant PF4(rPF4) as well as modified analogs (mutants) of PF4, and peptide fragments thereof, to inhibit angiogenesis. The modified PF4, analogs, and certain fragments are shown to have utility for treating angiogenic diseases and for the inhibition of endothelial cell proliferation. Also, the subject invention concerns modification of PF4 which facilitate the targeting of the biological activity of PF4 to specific locations.

18 Claims, 10 Drawing Sheets

Glu - Ala - Glu - Asp - Gly - Asp - Leu - Gln - Cys
                                                  10

Leu - Cys - Val - Lys - Thr - Thr - Ser - Gln - Val - Arg -
                                                        20

Pro - Arg - His - Ile - Thr - Ser - Leu - Glu - Val - Ile -
                                                        30

Lys - Ala - Gly - Pro - His - Cys - Pro - Thr - Ala - Gln -
                                                        40

Leu - Ile - Ala - Thr - Leu - Lys - Asn - Gly - Arg - Lys -
                                                        50

Ile - Cys - Leu - Asp - Leu - Gln - Ala - Pro - Leu - Tyr -
                                                        60

Lys - Lys - Ile - Ile - Lys - Lys - Leu - Leu - Glu - Ser - COOH ] rPF4
                                                              70

-Gln - Glu - Ile - Ile - Gln - Glu - Leu - Leu - Glu - Ser - COOH ] rPF4-24
  61                                                          70

REGION MODIFIED IN rPF4-241 MUTANT

FIG. 2

MODIFIED PF4 COMPOSITIONS AND METHODS OF USE

BACKGROUND OF THE INVENTION

Angiogenesis, the development of new capillary blood vessels, is an important process in the developing fetus and growing human. However, in healthy adults, angiogenesis occurs significantly only during wound healing and in the menstrual cycle.

It is now widely recognized that much of the aniogenic activity occurring in adults is pathological in nature. For example, proliferation of vascular endothelial cells and formation of new capillaries is essential for growth of solid tumors beyond a few cubic millimeters in volume (Folkman et al. [1983] Ciba Found. Symp. 100:132-149). We now understand that developing tumors secrete growth factors which stimulate neighboring endothelial cells to divide and migrate toward the tumor.

In addition to growth of solid tumors, other conditions involving angiogenic dysfunctions include diabetic retinopathy, retrolental fibroplasia, neovascular glaucoma, psoriasis, angiofibromas, immune and non-immune inflammation (including rheumatoid arthritis), capillary proliferation within atherosclerotic plaques, hemangiomas, and Kaposi's Sarcoma have also recently been recognized as diseases possessing characteristics of dysregulated endothelial cell division and capillary growth. These conditions along with growth of solid tumors are collectively referred to as "angiogenic diseases" (Folkman, J., and M. Klagsbrun [1987] Science 235:442-447).

In addition to angiogenic diseases, there are other conditions where endothelial cell proliferation is pathological or, at least, unwanted. For example, endometriosis is characterized by the abnormal proliferation and positioning of certain endothelial cells which normally line the inner wall of the uterus. Control of the angiogenic process could help to prevent or alleviate endometriosis. Also, prevention of endothelial cell growth in the uterus could be a means of birth control.

Endothelial cell growth is associated with wound healing. This growth is undesirable during extended surgical proceedings and where excessive scar formation may occur. Therefore, a means of controlling endothelial cell proliferation would help prevent or reduce unwanted scar formation.

The mechanism of angiogenesis and endothelial cell proliferation has not been completely characterized. It has been established that mast cells accumulate at a tumor site before new capillary growth occurs; however, mast cells alone cannot initiate angiogenesis. Heparin, a mast cell product, has been shown to significantly stimulate the capillary endothelial cell migration which is necessary for angiogenesis (Folkman, J. [1984] Angiogenesis: Initiation and Modulation. In *Cancer Invasion and Metastasis: Biologic and Therapeutic Aspects.* G. L. Nicolson and L. Milas, eds. Raven Press, New York, pp. 201-208).

Several substances are known to have the capability of inhibiting endothelial cell growth in vitro. One of the most extensively studied inhibitors of endothelial cell growth is protamine, which is a protein found only in sperm. Protamine has been shown to inhibit tumor angiogenesis and subsequent tumor growth (Taylor, S. and J. Folkman [1982] Nature 297:307-312). Protamine's anti-angiogenesis activity has been attributed to its well-known capacity to bind heparin (Taylor and Folkman [1982], supra). Clinical experiments with protamine have not been pursued because of the toxicity associated with protamine injection. Protamine, which is usually isolated from salmon sperm, is known to be antigenic in humans, and anaphylactic reactions to this protein have been observed with secondary exposures.

At least two other compounds have been studied in regard to their heparin-binding activity: platelet factor 4 (PF4) and major basic protein. Major basic protein has demonstrated heparin-binding activity but is of little practical utility because of its high toxicity.

Platelet factor 4 is a well-known protein which has been completely sequenced (Deuel, T. F., P. S. Keim, M. Farmer, and R. L. Heinrikson [1977] Proc. Natl. Acad. Sci. USA 74(6):2256-2258). It is a 70-residue secretable platelet protein with a molecular weight of approximately 7.8 Kd. Although there is evidence of heparin binding activity and some indications of anti-angiogenesis activity (Folkman [1984], supra), PF4 has never been shown to have clinical utility.

A compound which has been described as "oncostatin A," and which appears to be the same, or similar to, native PF4, has been implicated as effecting the growth of tumors (U.S. Pat. Nos. 4,645,828 and 4,737,580; both issued to Twardzik et al.). However, the effects reported in these patents pertain to slowly growing human cancer cells in immunodeficient mice. The results of these experiments cannot be reliably extrapolated to predict the effect of rapidly growing tumors which are native to the host animal. Furthermore, the experiments reported in these patents in no way predict or disclose any angiostatic properties.

Various peptides from PF4 have been purified and their properties studied. None has been shown to have any role in the inhibition of angiogenesis. It is known that the C-13 peptide of PF4 is chemotactic for neutrophils and monocytes (Deuel, T. F., R. M. Senior, D. Chang, G. L. Griffin, R. L. Heinrikson, and E. T. Kaiser [1981] Proc. Natl. Acad. Sci. USA 78:4585-4587; Osterman, D. G., G. L. Griffin, R. M. Senior, E. T. Kaiser, and T. H. Deuel [1982] Biochem. and Biophys. Res. Comm. 107(1):130-135). It is significant to note that the infiltration of monocytes would be expected to stimulate the proliferation and migration of local endothelial cells by the secretion of angiogenic factors. Thus, peptides of PF4 could be expected to stimulate, rather than inhibit, angiogenesis.

There is a significant and very long-standing need to locate an effective and non-toxic inhibitor of angiogenesis and endothelial cell proliferation. Angiogenesis plays a major role in the initiation and progression of widespread catastrophic illnesses, including cancer. An effective, non-toxic agent which can be administered locally and/or systemically to treat these illnesses would be highly advantageous and has long eluded identification.

BRIEF SUMMARY OF THE INVENTION

The subject invention relates to compositions obtained through chemical modifications of PF4 or recombinant PF4 (rPF4). For example, PF4 can be modified through its free amino groups with fluorescein-isothiocyanate and retain the capability of inhibiting angiogenic activity and endothelial cell proliferation. Similar modifications can be made with PF4 analogs, mutants, or fragments.

A further aspect of the subject invention is the targeting of the biological activity of PF4 to specific locations where that activity is needed. This can be done by conjugating PF4 (or an appropriate fragment, analog, or mutant) to a monoclonal or polyclonal antibody, carrier protein, cell receptor molecule, or other binding protein sequence. In addition to treating angiogenic disorders and inhibiting endothelial cell proliferation, modified PF4 can also be used to target toxins to specific cell populations. Various other modifications of PF4 and related compounds are described here. These modifications can be made in order to enhance biological activity or otherwise increase the utility of the PF4 compound.

BRIEF DESCRIPTION OF THE DRAWINGS

FIG. 2 compares the amino acid sequence of rPF4 with rPF4-241.

DETAILED DESCRIPTION OF THE INVENTION

Figure 1:
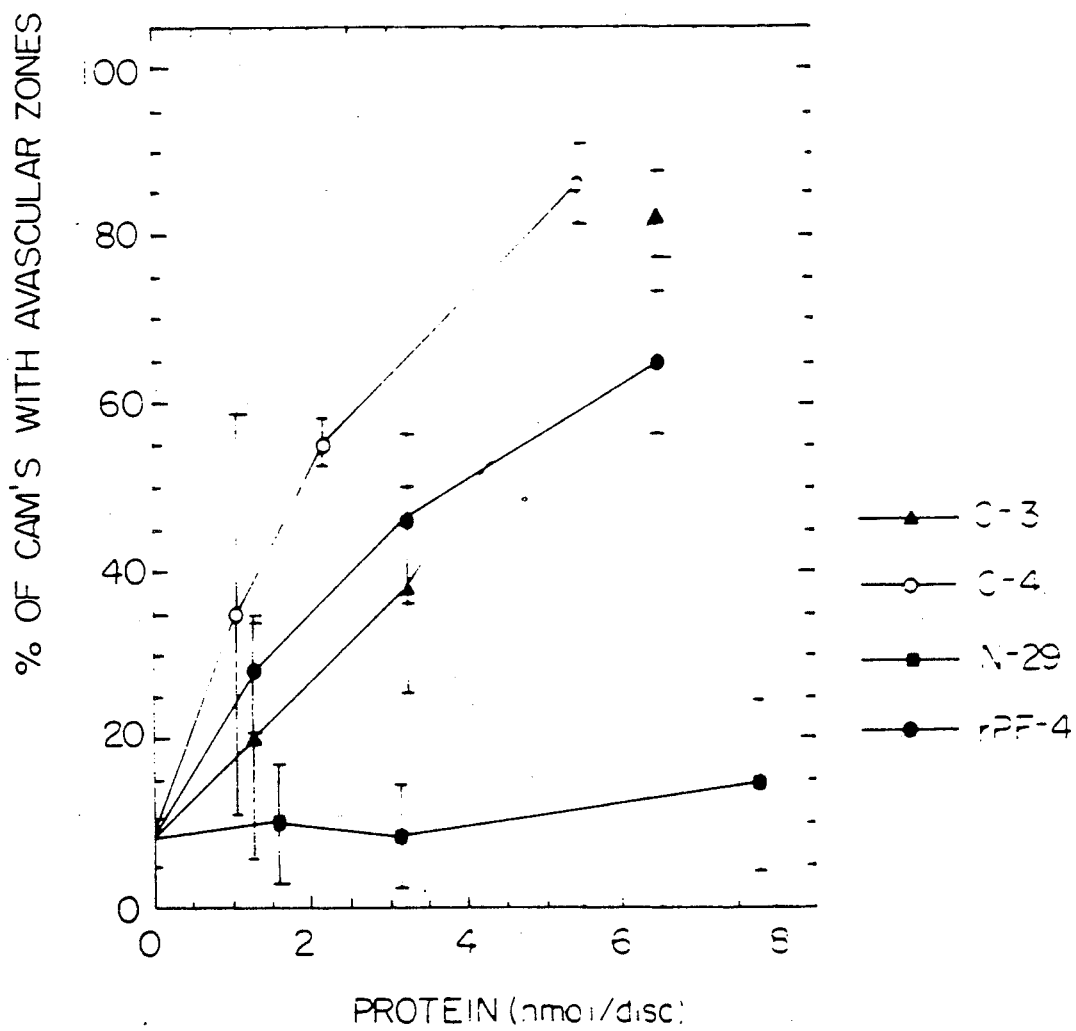
FIG. 1 shows the inhibition of angiogenesis resulting from treatment with rPF4 and various related peptides.

The subject invention concerns the discovery that PF4, rPF4, and fragments and analogs of these compounds can be chemically modified to create new compounds with highly desirable characteristics. For example, chemical modification of rPF4 and its fragments has resulted in the identification of compounds which show surprising ability to inhibit angiogenic activity as well as the capability to inhibit endothelial cell proliferation. One specific chemical modification which resulted in altered biological properties involved modification of the free amino groups of rPF4 with fluorescein-isothiocyanate (FITC). The resulting adduct, FrPF4, lacks heparin binding activity because of modification of lysine residues within the heparin binding domain but, surprisingly, retains the ability to inhibit angiogenesis as well as suppress HUVEC proliferation in vitro.

Angiostatic activity is also found in PF4 fragments and mutants which have been modified with the bulky and hydrophobic fluorescein moiety. In addition to their biological activity, the FITC-labeled PF4 sequences are useful for visual detection of PF4 molecules. Furthermore, the ability to modify PF4 and its fragments with large moieties without loss of the relevant biological activity provides a basis for conjugating PF4, its fragments, mutants, or derivatives with toxins, monoclonal antibodies, polyclonal antibodies, fluorophores, cell receptor molecules, non-proteinaceous biological effector molecules, chelators, carrier proteins, and other large entities.

One of the uses of the compounds described here is in the treatment of angiogenic diseases. As used in this application, the term "angiogenic disease" refers to growth of solid tumors, and other conditions involving angiogenic dysfunctions including diabetic retinopathy, retrolental fibroplasia, neovascular glaucoma, psoriasis, angiofibromas, immune and non-immune inflammation (including rheumatoid arthritis), capillary proliferation within atherosclerotic plaques, hemangiomas, and Kaposi's Sarcoma. The subject invention also concerns the use of rPF4 and PF4 fragments, analogs, and mutants for treatment of diseases of dysregulated endothelial cell proliferation.

As used in this application, the term "analog" refers to compounds which are substantially the same as another compound but which may have been modified by, for example, adding additional amino acids or side groups. "Mutants" as referred to in this application refers to amino acid sequences which are substantially the same as another sequence but which have different amino acids at certain locations in the amino acid sequence. "Fragments" refer to portions of a longer amino acid sequence.

The subject invention embraces the specific amino acid sequences and other compositions which are specifically exemplified. The subject invention further embraces analogs and mutants of these sequences, as well as fragments of the sequences, and analogs and mutants of the fragments. These analogs, mutants, and fragments are embraced within the subject invention so long as the analog, fragment, or mutant retains substantially the same relevant biological activity as the originally exemplified compound. For example, it is well within the skill of a person trained in this art to make conservative amino acid substitutions. These substitutions are discussed in more detail below. To the extent that these substitutions do not substantially alter the relevant biological activity, then the resulting compounds fall within the scope of the subject invention. The term "relevant biological activity" refers to the activity of interest for a particular application of a compound. For example, several uses of PF4 are discussed below. These uses include inhibition of angiogenesis and endothelial cell proliferation. When PF4 is being used in these ways then "analogs" would refer to compounds where PF4 has been modified (by a conservative amino acid substitution, for example) without substantially altering the compound's ability to inhibit angiogenesis or endothelial cell proliferation. Conservative amino acid substitutions are only one example of the type of modifications which are within the scope of the subject matter of this invention.

The subject invention arises from the unexpected discovery that chemically modified rPF4 inhibits in vivo capillary formation and embryonic neovascularization. It has also been determined that full length recombinant PF4 inhibits growth factor-dependent human endothelial cell proliferation in vitro. Significantly, it has also been determined that the angiogenesis-inhibiting activity of PF4 is retained by synthetic peptides corresponding to sequences of PF4 as small as 13 amino acids in length. In particular, a synthetic peptide of 13 amino acids corresponding to the carboxy terminus of PF4 (C-13) has displayed potent angiostatic activity.

The activity of the C-13 peptide is especially surprising in light of its inability to affect the anticoagulant activity of heparin. The use of the C-13 peptide offers several advantages over whole rPF4 such as reduced dosage (weight basis), reduced likelihood of antigenicity, and greater likelihood of effectiveness in novel dosage forms.

The C-13 peptide of PF4 also retains the ability to prevent Con-A induced immunosuppression in mice, an activity which is unaffected by heparin and probably independent of the ability of the peptide to inhibit angiogenesis.

It is well understood that angiogenesis is required for solid tumors to grow beyond a few cubic millimeters. Thus for the treatment of solid tumors, use of rPF4, or modifications thereof, to cause tumor rejection by inhibiting angiogenesis presents a novel and highly advantageous means of therapy. The fact that the C-13 peptide inhibits angiogenesis without affecting the anticoagulant activity of heparin demonstrates that this small peptide would also have the benefit of not interfering with concurrent anticoagulant therapy. Additionally, small peptides are generally less antigenic than larger proteins, and, thus, the PF4 fragments can be used advantageously for oral and transdermal administration. These types of delivery are particularly useful in the treatment of gastrointestinal capillary proliferation (e.g., Kaposi's Sarcoma) and skin lesions, respectively. Intralesional, as well as systemic, administration of PF4 fragments are also appropriate for treatment of these conditions. Topical or aerosol administration of PF4 fragments is appropriate for skin or pulmonary lesions, respectively (e.g., Kaposi's sarcoma and lung cancer).

An analog of PF4 which exhibits enhanced ability to inhibit angiogenesis has been synthesized. This analog, known as rPF4-241, was created by cassette mutagenesis of a synthetic PF4 gene whereby four lysine residues of the carboxy terminus of PF4 were converted to two Gln-Glu couplets in order to eliminate heparin binding activity while retaining the $\alpha$-helical secondary structure. If rPF4-241 (or FrPF4-241) is administered intralesionally, it can be applied such that the dosage is between about 1 $\mu$g/lesion and about 4 mg/lesion. For systemic administration, the dosage of rPF4-241 (or FrPF4-241) can be between 0.5 mg/kg of body weight and about 100 mg/kg of body weight. Similar and higher dosages can be used for the administration of native sequence rPF4 (or FrPF4) as well as peptide fragments. For example, dosages of rPF4 (or FrPF4) and fragments thereof may be twice that of rPF4-241 (or FrPF4-241) or higher.

The compounds of the subject invention can be combined with a suitable pharmaceutical carrier. For example, FrPF4 or FrPF4-241 can be formulated in physiologically acceptable carriers, such as phosphate buffered saline, distilled water, excipients, or the like, or may be administered neat.

MATERIALS AND METHODS

Chicken Chorioallantoic Membrane (CAM) Assay. Fertile eggs were incubated in a stationary position for 3 days at 37° C. and 70-80% relative humidity. During this time, the embryo rose to the upper surface of the egg contents. At the beginning of the 4th day, the eggs were cracked without inversion and carefully deposited into sterile plastic petri dishes such that the embryo remained on the upper surface. The shell-free eggs were incubated for an additional 72 hours at 37° C., under an atmosphere containing 2.5-3.5% $CO_2$ after which the growing embryos developed a recognizable CAM. Discs, made by mixing test samples with 1% (w/v) methylcellulose were dried and placed on the CAM between major veins and approximately 0.5 cm from the embryo. Following another 48 hour incubation at 37° C. (2.5-3.5% $CO_2$), the samples were scored for their ability to inhibit angiogenesis. Inhibition appears as an avascular zone surrounding the implant and can often include elbows formed by veins avoiding the disc and a reduced number of capillaries in the region of the implant.

Endothelial Cell Proliferation Assay. Human umbilical vein endothelial cells were cultured in Medium 199 (Gibco) containing 10% (v/v) fetal bovine serum (FBS), 150 mcg/ml endothelial cell growth supplement (ECGS) and 5 units/ml heparin at 37° C. and 4-5% $CO_2$. Every 3-4 days, the cultures were harvested by trypsin treatment, diluted, replated, and grown to confluence. Prior to the start of an experiment, the cells were centrifuged and resuspended in heparin-free media and incubated with the test substance for 3 days under standard culture conditions. At the end of the incubation period, the cells were harvested and counted. Statistical significance between means was determined by a standard Student t-test for unpaired data.

rPF4 Production. Recombinant PF4 was produced in E. coli as an N-terminal fusion protein containing a methionine immediately preceding the PF4 sequence. The insoluble fusion protein was cleaved with cyanogen bromide treatment and purified by heparin agarose affinity chromatography. The isolated protein was buffer exchanged into 20 mM sodium acetate, pH 4.0, and either frozen or lyophilized for storage.

Production of Peptides. Peptides were prepared by standard solid phase synthesis procedures, cleaved from the solid support and deblocked, and purified by reverse phase HPLC.

Following are examples which illustrate procedures, including the best mode, for practicing the invention. These examples should not be construed as limiting. All percentages are by weight and all solvent mixture proportions are by volume unless otherwise noted.

EXAMPLE 1

Chicken eggs, prepared as described above, were treated with discs containing several concentrations of recombinant PF4 or peptides derived from the sequence of PF4. rPF4 and C-terminal peptides as small as 13 amino acids inhibited angiogenesis on the CAM (FIG. 1). In each case, the inhibition was dose-dependent and the response approximately equivalent (molar basis) for the inhibitors containing the C-terminal region of PF4. An N-terminal peptide of PF4 (N-29) did not inhibit angiogenesis even at the highest concentration tested, suggesting that all of the anti-angiogenic activity of PF4 is probably associated with the C-terminal portion of the molecule. Since the C-terminus of PF4 is rich in lysine, polylysine was tested in this assay system and found not to cause inhibition at 6.5 nmol dosages.

EXAMPLE 2

The lysine rich region of PF4 (residues 61-66) is also the domain associated with the binding of heparin by PF4. Heparin is known to play a role in modulating angiogenesis, which can also be affected by protamine, another well characterized heparin-binding protein. To assess the ability of PF4-based synthetic peptides to bind heparin, we assayed the activity of coagulation-cascade enzymes which are inhibited by heparin. Protamine and platelet factor 4 are able to prevent the heparin inhibition of thrombin and Factor Xa at approximately equimolar concentrations. The 41 amino acid C-terminal peptide of PF4 (C-41) prevented heparin inhibition less effectively, but the C-13 peptide was unable to prevent the inhibition of thrombin even at concentrations ten times that of an effective level of rPF4. This unexpected finding suggests that the C-13 peptide inhibits angiogenesis by some method other than heparin binding.

EXAMPLE 3

Many angiostatic agents act by direct inhibition of endothelial cell proliferation. Endothelial cell division and growth is tightly controlled and strictly dependent on the presence of growth factors. We evaluated the ability of rPF4 and related peptides to inhibit growth factor-stimulated human endothelial cell proliferation in vitro. rPF4 significantly inhibited endothelial cell growth in a dose-dependent fashion at a concentration as low as 10 mcg/ml. Inhibition was complete at 25 mcg/ml in the heparin-deficient medium employed here.

EXAMPLE 4

To assess the importance of the heparin binding activity of PF4 in the inhibition of endothelial cell proliferation, cells were incubated in media containing or lacking 5 units/ml heparin. The presence of heparin stimulated proliferation of these cells during the three day incubation of this experiment. rPF4 significantly inhibited both control (100%) and heparin stimulated (45%) endothelial cell growth (Table I).

TABLE 1

| | Attenuation of rPF4 inhibition of endothelial cell growth by heparin. | | |
|---|---|---|---|
| | rPF4 | | % |
| Addition | — | 50 mcg/ml | Inhibition[a] |
| — | 14.4 ± 2.5 | [b]6.0 ± 0.6 | ~100 |
| 5 u/ml heparin | 18.9 ± 1.2 | [b]14.0 ± 0.4 | 45 |

[a]Based on seeding of 8 × 10⁴ cells/well
[b]Significantly different from appropriate control (p < 0.005)

EXAMPLE 5

Construction of rPF4-241

Figure 3:
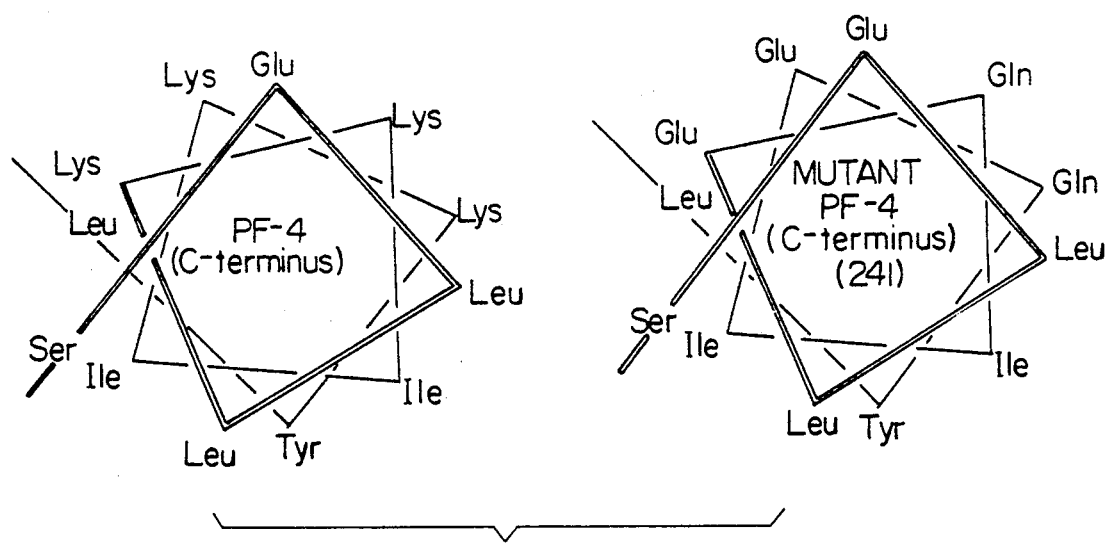
FIG. 3 depicts the α-helical configurations of rPF4 and rPF4-241.

Cassette mutagenesis of a synthetic PF4 gene was used to convert the four lysine residues at the carboxy terminus of PF4 to two Gln-Glu couplets (see FIG. 2). This construction apparently retains the α-helical secondary structure (FIG. 3) for this region of the molecule with the concurrent loss of heparin binding activity.

The gene for rPF4-241 was expressed as a fusion protein in E. coli with the same N-terminal amino acid sequences as with the parent rPF4 molecule. The protein was cleaved from the E. coli fusion peptide by CNBr and formic acid and purified to near homogeneity by DEAE-sepharose chromatography. The protein was reactive with polyclonal antibodies to PF4 and was determined to possess the appropriate modifications by amino acid analysis. Significantly, the purified mutant protein lacked heparin-binding activity in the Factor Xa inhibition assay.

The substitutions described here can be made with the peptide fragments as well as with the full length PF4 molecule. For example, C-13-241 has the following sequence:
Pro-Leu-Tyr-Gln-Glu-Ile-Ile-Gln-Glu-Leu-Leu-Glu-Ser

EXAMPLE 6

Inhibition of angiogenesis by rPF4-241

Figure 4:
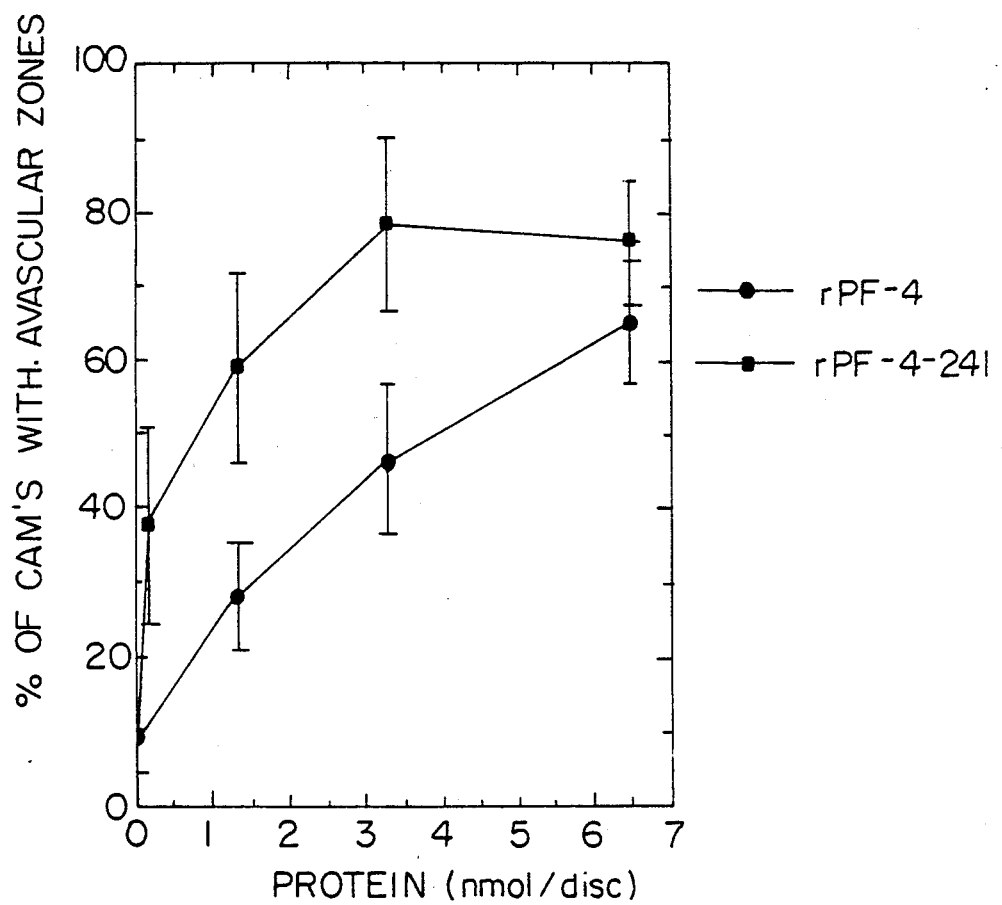
FIG. 4 compares the inhibition of angiogenesis resulting from treatment with rPF4 and rPF4-241.

Purified rPF4-241 was dried in methylcellulose discs and tested for its ability to inhibit capillary growth in the chicken chorioallantoic membrane (CAM) assay. Even at the lowest concentrations tested (1.25 nmol/disc) rPF4-241 extensively inhibited angiogenesis in the CAM system (FIG. 4). This inhibition was even more effective than that caused by equal concentrations of native rPF4 as suggested by larger avascular zones on the membrane. The inhibitory effect of rPF4-241 was not reversed by heparin.

EXAMPLE 7

Inhibition of human endothelial cell proliferation by rPF4-241

Figure 5:
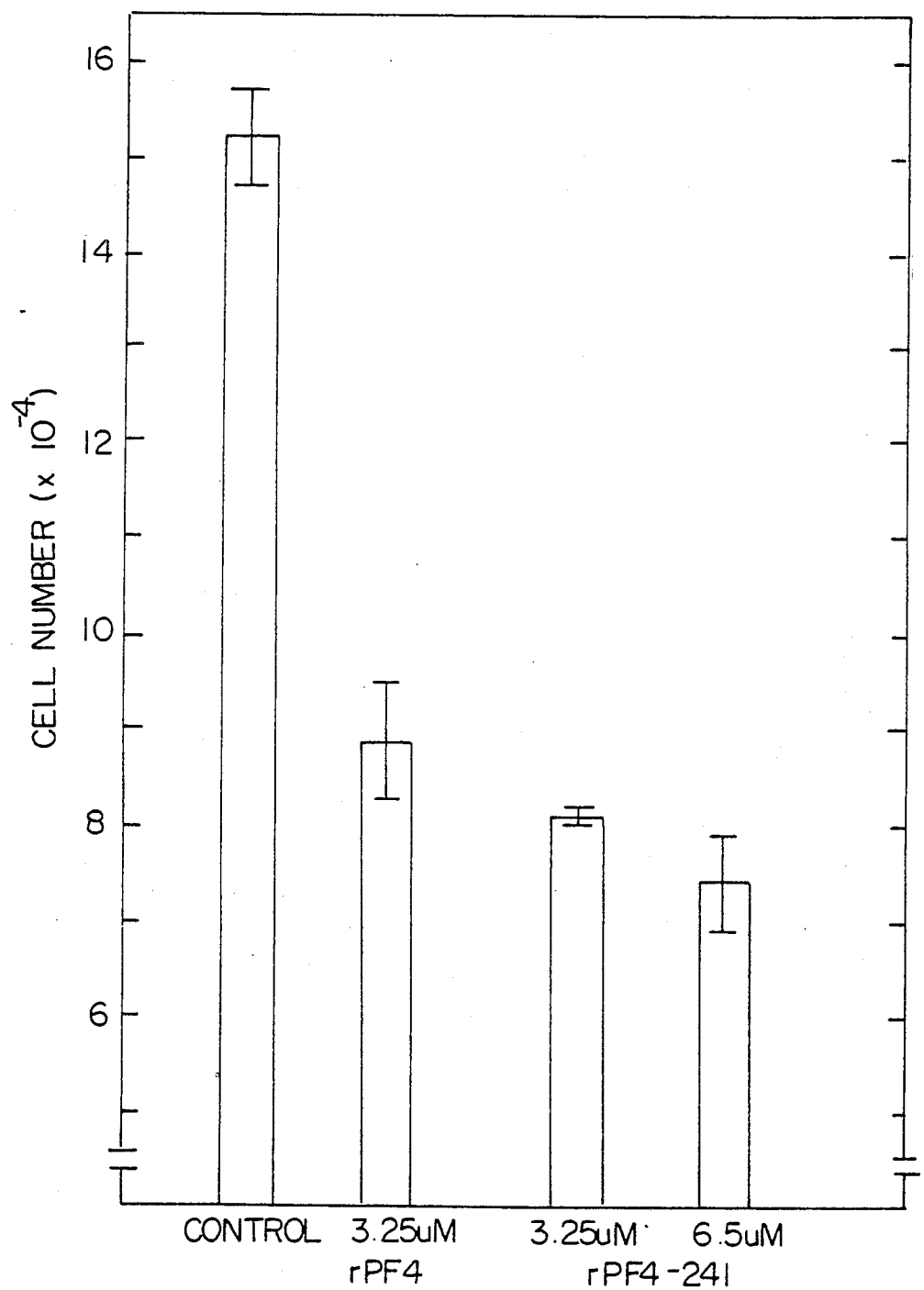
FIG. 5 shows inhibition of human endothelial cell proliferation by rPF4 and rPF4-241.

At concentrations where native rPF4 completely inhibits endothelial cell proliferation, mutant rPF4-241 was at least as effective in inhibiting cell growth (FIG. 5). Further tests suggest that rPF4-241 was inhibitory at concentrations as low as 0.5 mcg/mL, a level at which native rPF4 has little or no effect.

Figure 6:
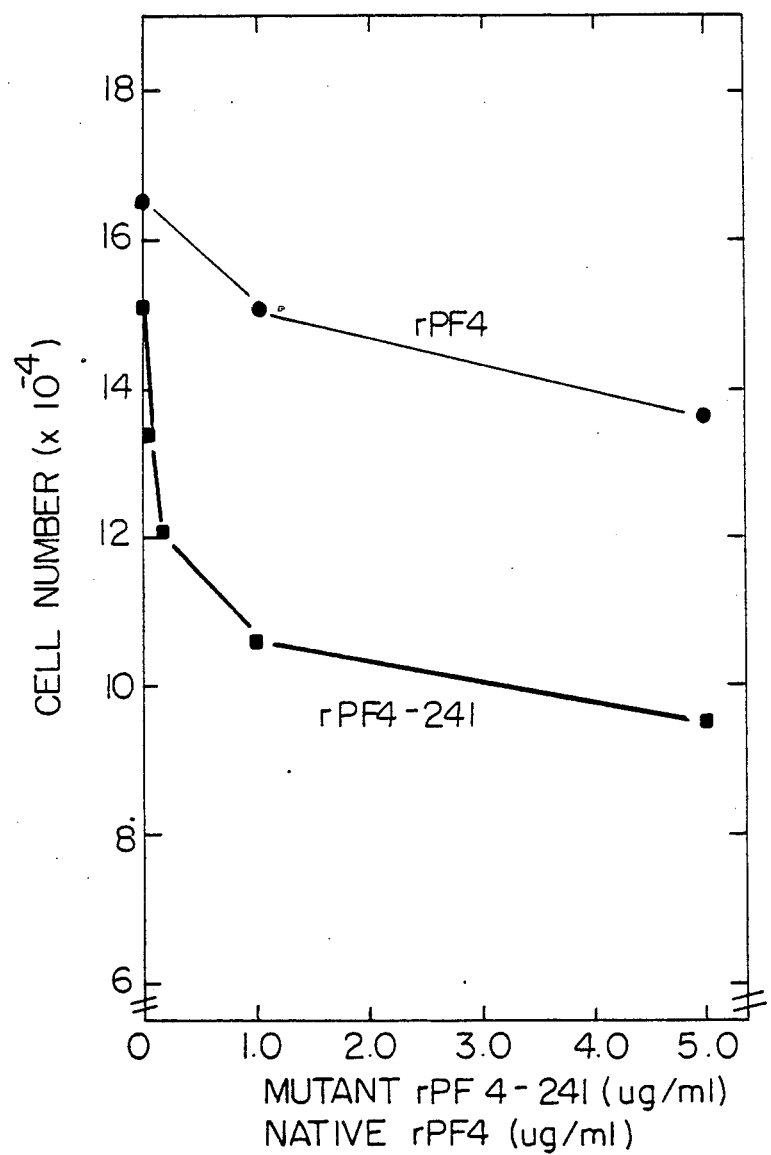
FIG. 6 compares the inhibition of human umbilical vein endothelial cell proliferation resulting from treatment with rPF4 or rPF4-241.

In a test of inhibition of human umbilical vein endothelial cell proliferation by native rPF4 and mutant rPF4-241, the rPF4-241 was shown to be much more effective than the native rPF4 at inhibiting the proliferation of these cells. The results of this test are shown in FIG. 6.

These results are remarkable in that previous theories of PF4 inhibition of angiogenesis assumed that the PF4 effects were due to heparin binding. We have designed a protein, retaining most of the structural features of native PF4 but lacking detectable heparin binding activity, which is apparently more active than native PF4 in inhibiting angiogenesis in vivo and endothelial cell proliferation in vitro. Additionally, the mutant we have designed would not be expected to interfere with heparin anticoagulant therapy.

EXAMPLE 8

Inhibition of In Vivo Tumor Growth

Normal C57BL/6J female mice (6–8 weeks old) were inoculated subcutaneously with $5 \times 10^5$ log phase cells of a B16-F10 melanoma tumor line. This protocol led to progressive tumor growth resulting in large (300 mm³) necrotic tumors after approximately 10 days, followed by death of untreated animals usually within three weeks of tumor inoculation.

In an experiment to test the efficacy of rPF4 in preventing in vivo tumor growth and angiogenesis, tumor bearing animals were divided into two groups. One group was injected with 50 μg rPF4 (native sequence) in 100 μl of 50 mM sodium phosphate, pH 6.5, 50 mM sodium chloride directly into the nascent tumor, daily, beginning one day after tumor inoculation. A control group was treated identically with carrier buffer lacking rPF4. Tumor volume was measured at regular intervals with digital calipers by laboratory personnel uninformed of the specific treatment received by each subject animal.

Figure 7:
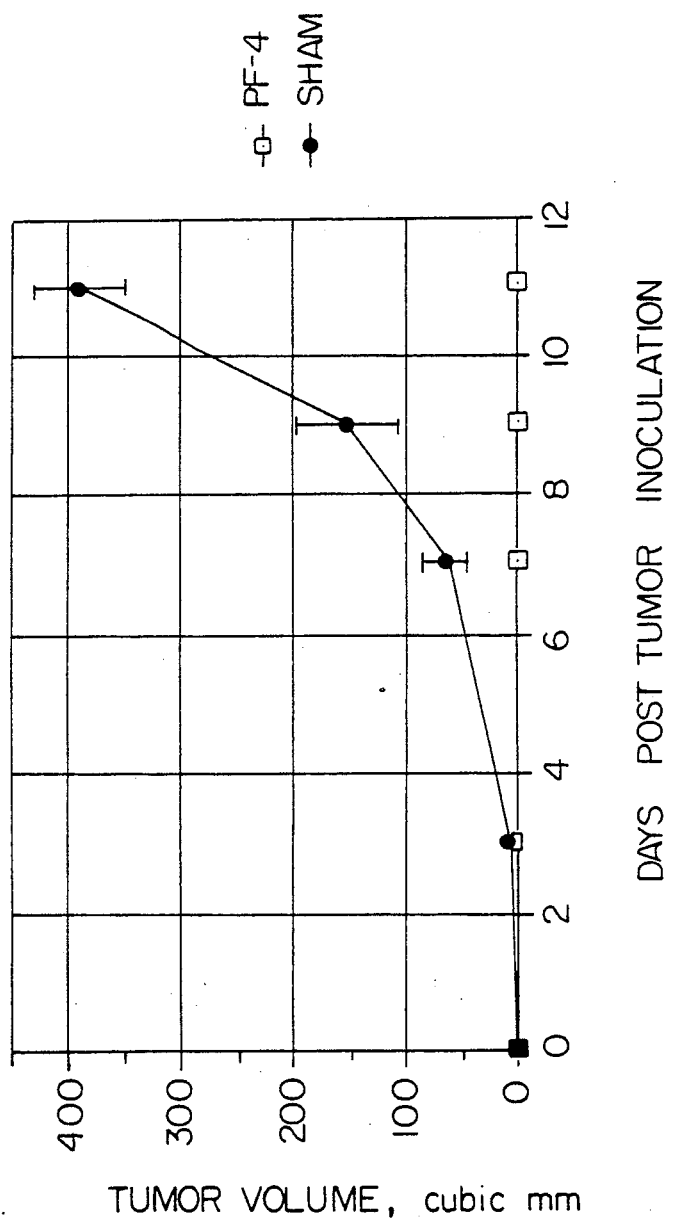
FIG. 7 shows the ability of rPF4 to inhibit tumor growth.

Within seven days of tumor inoculation, control animals possessed obvious three dimensional tumors, while rPF4-treated animals were essentially tumor-free (FIG. 7). Continued treatment with rPF4 completely suppressed tumor growth under these conditions where control animal tumors became necrotic and large as seen previously with untreated mice. The same effect was observed when rPF4-241 was used as the inhibitory agent.

This finding supports the proposition that rPF4, as an inhibitor of angiogenesis, will possess clinical usefulness in the management of malignant melanoma and other cancers. Progressive growth of tumors requires new blood vessel formation which, if inhibited, may not only restrict tumor growth, but stimulate regression of existing vessels, as well as enhance other responses to malignant invasion.

The finding that rPF4 inhibition of in vivo tumor growth was apparent within three days of the initial inoculation (of rPF4) indicates that rPF4 acts to modulate tumor growth by local mechanisms rather than by immunomodulation which would require a longer time course. Additionally, rPF4 did not directly inhibit tumor cell growth in vitro. It appears, therefore, that rPF4 was modulating the host's angiogenic response to the growing tumor.

It has been shown that proteins of identified structure and function may be constructed by changing the amino acid sequence if such changes do not alter the protein secondary structure (Kaiser, E. T., and F. J. Kezdy [1984] Science 223:249–255). Thus, the subject invention includes mutants of the amino acid sequences depicted herein which do not alter the protein secondary structure, or if the structure is altered, the biological activity is retained. In particular it should be understood that conservative substitutions of amino acids may be made. For example, amino acids may be placed in the following classes: basic, hydrophobic, acidic, polar, and amide. Substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Example of Amino Acids |
|---|---|
| Basic | Lys, Arg, His |
| Hydrophobic | Leu, Ile, Val, Phe, Trp |
| Acidic | Glu, Asp |
| Polar | Ser, Thr |
| Amide | Gln, Asn |

In some instances, non-conservative substitutions can also be made. For example, lysine may be substituted for with any of the following amino acids: Glu, Gln, Asp, Asn, Met, Ala, Leu, and Ile. The critical factor is that these substitutions must not significantly detract from the biological activity of the rPF4 or the rPF4 fragment.

EXAMPLE 9

Modification of PF4 and rPF4-241 with Fluorescein-Isothiocyanate (FITC)

Figure 8:
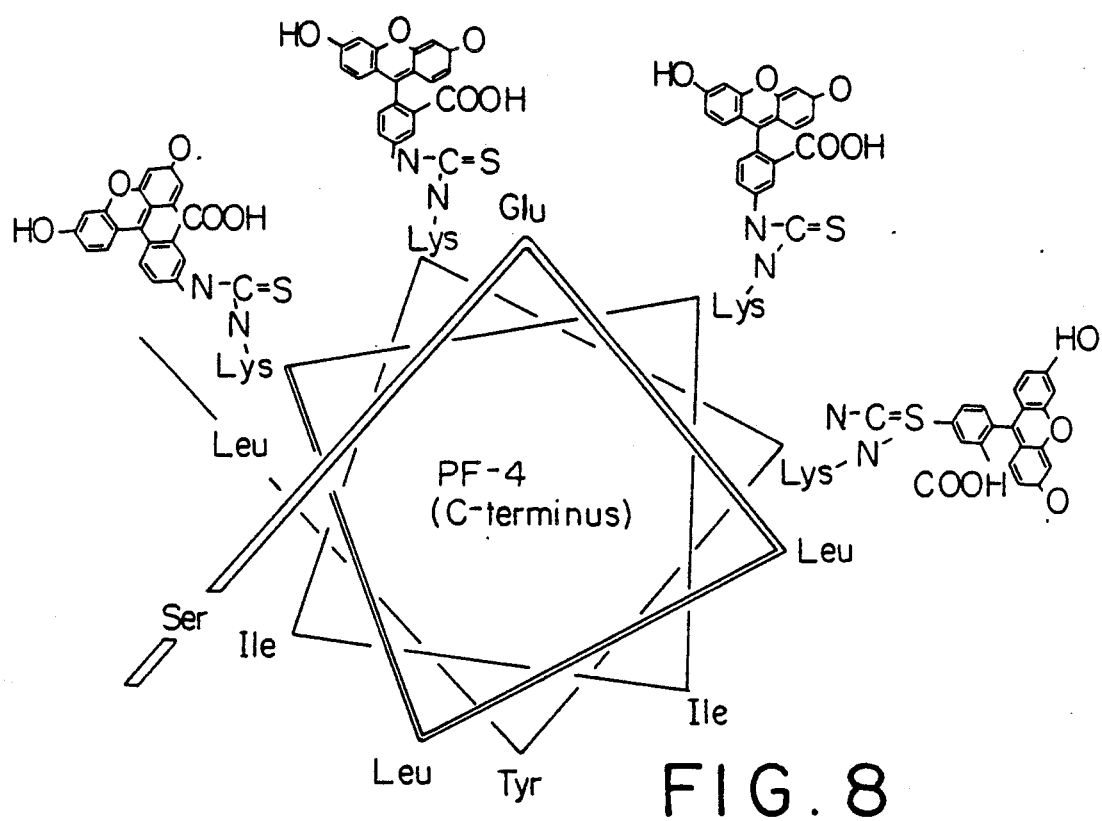
FIG. 8 depicts the possible chemical structure of the C-terminal end of FrPF4.

Purified rPF4 or rPF4-241 (5 mg in 50 mM $Na_2CO_3$, pH 9.3, 25 mM NaCl) was treated with 5 mg of fluorescein isothiocyanate in a volume of 5 ml to modify the free amino groups. After incubation for 3 hours at room temperature in the dark, the labeled protein (FrPF4 or FrPF4-241) was separated from unbound FITC by gel filtration and dialyzed into 50 mM acetic acid. A possible structure of the C-terminus of FrPF4 is shown in FIG. 8.

EXAMPLE 10

Inhibition of Angiogenesis by Fluorescein-Isothiocyanate-Conjugated rPF4

FrPF4 was tested for activity in the CAM assay as described above. Although FrPF4 lacked heparin binding activity, it retained full activity as an inhibitor of angiogenesis on the CAM. The results of these assays are shown in Table 3.

TABLE 3

| Activity of FrPF4 in the CAM assay. | | |
|---|---|---|
| Amount per | Inhibition (%) | |
| disc (µg) | rPF4 | FrPF4 |
| 0 | 0 | 0 |
| 10 | 22 | 17 |
| 25 | 33 | 33 |

EXAMPLE 11

Inhibition of Endothelial Cell Proliferation by FrPF4 and FrPF4-241

FrPF4 and FrPF4-241 were tested separately to determine their ability to inhibit endothelial cell proliferation. HUVE cells were tested for their sensitivity to FrPF4 as described above except that [$^3$H]-thymidine was added to the cultures 24 hours after the addition of FrPF4. The cultures were then incubated an additional 6 hours. Cells were harvested, washed, and radioactive thymidine incorporation into DNA was measured.

Figure 9:
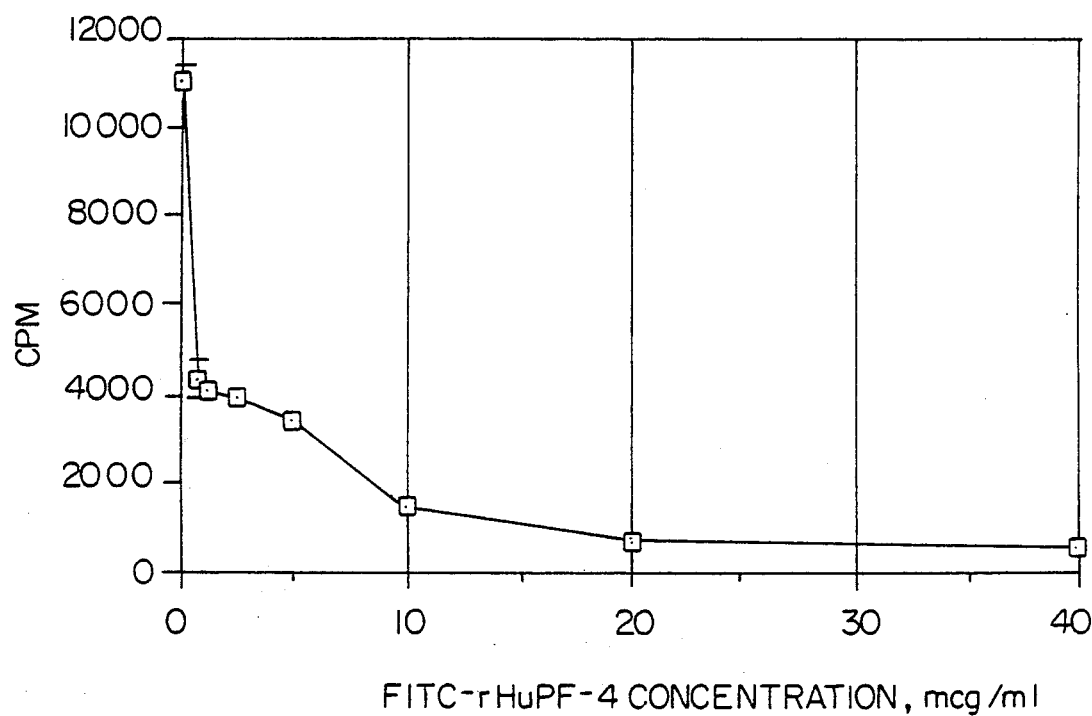
FIG. 9 shows inhibition of human endothelial cell proliferation by FrPF4.
Figure 10:
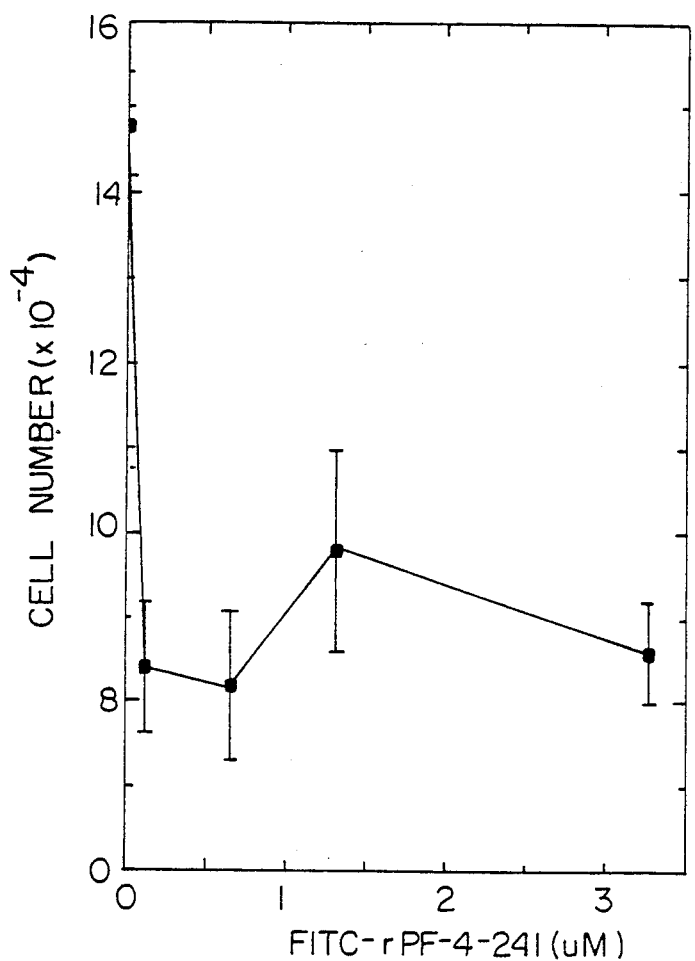
FIG. 10 shows inhibition of human endothelial cell proliferation by FrPF4-241.

As shown in FIG. 9, FITC-conjugated rPF4 was very effective, even at low dosages, in inhibiting DNA synthesis in human umbilical vein endothelial cells and therefore inhibiting cell proliferation. Similar results were obtained using FrPF4-241. In this case, the inhibition of HUVE cell proliferation with increasing concentrations of rPF4-241 was tested using the Endothelial Cell Proliferation Assay as described above. The results of experiments using FrPF4-241 are shown in FIG. 10.

EXAMPLE 12

Inhibition of In vivo Tumor Growth by FITC-rPF4

Figure 11:
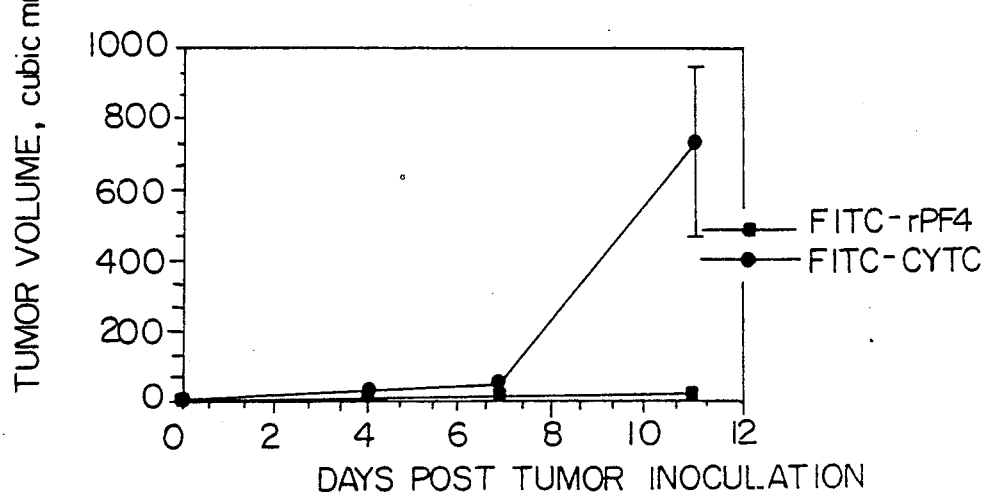
FIG. 11 shows inhibition of tumor growth by FrPF4.

B-16 Melanoma tumors were grown in C57BL6/J mice as described previously. Treatment was begun 24 hours following implantation of tumor cells (Day 1) and consisted of 25 µg/day of FrPF4 in 100 µl of sodium acetate buffer, pH 4.0. Control mice were injected with 25 µg/day of FITC labeled cytochrome-C in the same buffer. A statistically significant suppression of tumor growth by FrPF4 was observed by Day 11 (FIG. 11).

EXAMPLE 13

Delivery of PF4 Activity to Specific Sites

For treatment of certain conditions, it is sometimes advantageous to direct biological activity to a specific location. For example, in order to inhibit solid tumor growth, it may be desirable to send PF4, or an analog with angiostatic properties, directly to the tumor site. This can be accomplished by coupling the PF4 (or analog) to an appropriate antibody, preferably a monoclonal antibody. The monoclonal antibody, which can be produced using techniques that are well-known in the art, will selectively seek out the target site. As the antibody moves to the desired location, it brings with it the PF4. Thus, the PF4 activity can be concentrated at a specific location.

General means of conjugating antibodies to polypeptides such as PF4 are well known to those skilled in the art and are discussed, for example, in U.S. Pat. Nos. 4,671,958 (Rodwell et al.) and 4,792,447 (Uhr et al.). The PF4 may also be targeted to specific locations via analogous conjugation with binding proteins (e.g., thrombospondin or fibroblast growth factor), cell receptor molecules (e.g., CD4, lymphocyte function associated antigen-1 [LFA-1], and von Willebrand Factor [vWF]) or the complementary ligands, and non-proteinaceous biological effector molecules (e.g., ICAM-1, tumor associated-antigens, and prostaglandins).

For example, the monoclonal antibody, or other moiety, can be associated with PF4 at one or both pairs of lysine residues located near the carboxy terminus of PF4. By associating the monoclonal antibodies as these residues, the angiostatic activity is retained while heparain binding is eliminated. Also, other amino acid residues may be substituted for the lysine residues before conjugation with appropriate moieties at these and other positions. Therefore, the compounds described here can be represented as follows:

$$\text{A Pro Leu Tyr } \overset{F}{\underset{|}{B}} \overset{G}{\underset{|}{C}} \text{ Ile Ile } \overset{H}{\underset{|}{D}} \overset{I}{\underset{|}{E}} \text{ Glu Ser COOH}$$

where:
(a) A represents all or part of the polypeptide sequence consisting of residues 1 through 57 of PF4; A may or may not be present on said hybrid polypeptide;
(b) B, C, D, and E can be any amino acid; and
(c) F, G, H, and I are selected from the group consisting of monoclonal antibodies, polyclonal antibodies, fluoresceinisothiocyanate, fluorophores, toxins, cell receptor molecules, non-proteinaceous biological effector molecules, and chelators; at least one of the moieties designated F, G, H, and I must be present on said hybrid polypeptide.

In the above representation of the compounds described here, the vertical lines represent chemical bonding interactions as do the spaces between the amino acids on the horizontal line. The existence of specifically illustrated moieties associated at B, C, D, and E does not exclude the possibility of conjugation occurring at other residues.

EXAMPLE 14

Conjugation of Carrier Proteins to PF4

It may be desirable to increase the circulating half-life of PF4 to improve its effectiveness as a systemically active angiostatic complex for tumor and angiogenic disease therapy. For example, PF4 can be crosslinked to a large carrier protein, e.g., human serum albumin (HSA) or immunoglobulin, by disuccinimidyl suberate (DSS) through free primary amino groups (i.e., lysine E-amino groups or N-terminal α-amino groups; see Montesano et al. [1982] Biochem. Biophys. Res. Comm. 109:7-13).

Purified rPF4 and HSA (10 mg and 100 mg, respectively) were incubated with 25 mM DSS for 4 hours at room temperature. The reaction was terminated by the addition of Tris buffer, pH 8.0 to a final concentration of 100 mM. The resulting composition was a heterogenous mixture of crosslinked molecules which lacked heparin binding activity, but retained the ability to inhibit HUVEC proliferation. A control sample in which HSA was crosslinked to cytochrome-C did not inhibit HUVEC growth.

EXAMPLE 15

Delivery of Toxin Molecules to PF4 Specific Targets

It is sometimes advantageous to use PF4 as the targeting molecule for directing the activity of a toxic agent to a particular cell type. For example, PF4 can be chemically or genetically crosslinked to the toxin ricin A or the diphtheria toxin.

A fusion protein comprised of PF4 and ricin A can be produced recombinantly in a prokaryotic or eukaryotic host. The resulting purified toxin will have the high specificity for endothelial cells or cells in close proximity to endothelial cells, e.g., tumor cells. Alternatively, PF4 and ricin can be linked with cross linkers. DSS can cross link PF4 and ricin A while retaining both PF4 and ricin A activities.

PF4 can also be covalently linked with a cross linker to photoactivatable molecules, for example, hematoporphyrin derivative (HPD). Water soluble carbodiimides (e.g., EDC) are most useful in linking the acid side chains of HPD to the amino groups of PF4. The resulting conjugate will concentrate at sites rich in endothelial cells (such as solid tumors) and can be activated by relatively non-toxic laser or phototherapy focused directly on the tumor site. Activated HPD is known to generate active oxygen species which non-specifically kill nearby cells.

EXAMPLE 16

Modification of the Cysteine Residues of rPF4

During preparation, the disulfides of rPF4 are reduced by dithiothreitol (DTT) to free sulfhydryls, but the heparin binding activity is retained. To assess the biological activity of PF4 requires removal of the DTT which, by allowing the disulfide bridges to reform, obscures whether or not they are essential for these activities.

The sulfhydryls of rPF4 were specifically and irreversibly modified by prereduction with DTT followed by treatment with fluorescein maleimide (FM). The reduced and purified rPF4 (5 mg in sodium carbonate buffer, pH 8.5 [SCB]) was treated with 10 mg of FM for 3 hours at room temperature. Residual FM was removed by gel filtration in SCB and then dialyzed against the same buffer. The FM-rPF4 partially retained heparin binding activity. When tested in the CAM and endothelial cell proliferation assays, FM-rPF4 exhibited inhibitory activity indicating that neither free sulfhydryls nor correct disulfide bonds are required for the angiostatic activity of PF4.

This FM-modified rPF4 may possess some utility as an alternative endothelial cell labeling or inhibiting compound but, most importantly, it indicates that the cysteine residues of PF4 are also appropriate targets for conjugating or cross linking PF4 to other molecules for diagnostic or therapeutic applications.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A substantially pure polypeptide conjugate free of other platelet proteins comprising:
   (a) a mutant polypeptide of native PF4, comprising the sequence Gln-Glu-Ile-Ile-Gln-Glu-Leu-Leu-Glu-Ser wherein said mutant polypeptide has angiogenic inhibitory activity; and
   (b) an entity which is conjugated to said mutant polypeptide,
wherein said conjugate retains angiogenic inhibitory activity.

2. The polypeptide conjugate, according to claim 1, wherein said conjugated entity comprises fluorescein-isothiocyanate or is otherwise the result of treating said mutant polypeptide with fluorescein-isothiocyanate.

3. The polypeptide conjugate, according to claim 1, wherein said conjugated entiry is a fluorophore.

4. The polypeptide conjugate, according to claim 1, wherein said conjugated entity is a toxin.

5. The polypeptide conjugate, according to claim 4, wherein said toxin is the diphtheria toxin or ricin A.

6. The polypeptide conjugate, according to claim 1, wherein said conjugated entity is an antibody.

7. The polypeptide conjugate, according to claim 1, wherein said conjugated entity is a carrier protein.

8. The polypeptide conjugate, according to claim 7, wherein said carrier protein is human serum albumin.

9. The polypeptide conjugate, according to claim 3, wherein said conjugated entity is a chelator.

10. The polypeptide conjugate, according to claim 1, wherein said mutant polypeptide and said conjugated entity are linked with a cross linker.

11. The polypeptide conjugate, according to claim 10, wherein said cross linker is disuccinimidyl suberate.

12. The polypeptide conjugate, according to claim 10, wherein said cross linker is a water soluble carbodiimide.

13. A pharmaceutical composition for the treatment of angiogenic diseases, said composition comprising a substantially pure polypeptide conjugate free of other platelet proteins, wherein said polypeptide conjugate comprises:
   (a) a mutant polypeptide of native PF4, comprising the sequence Gln-Glu-Ile-Ile-Gln-Glu-Leu-Leu-Glu-Ser, wherein said mutant polypeptide has angiogenic inhibitory activity; and
   (b) an entity which is conjugated to said mutant polypeptide,
wherein said conjugate retains angiogenic inhibitory activity.

14. A process for inhibiting angiogenesis, said process comprising the administration of an effective amount of a polypeptide conjugate of claim 1.

15. A method for delivering angiogenic inhibitory activity to cells in need of treatment, said method comprising the administration of a composition comprising a substantially pure polypeptide conjugate free of other platelet proteins comprising:
   (a) a mutant polypeptide of native PF4, comprising the sequence Gln-Glu-Ile-Ile-Gln-Glu-Leu-Leu-Glu-Ser, wherein said mutant polypeptide has angiogenic inhibitory activity; and
   (b) an entity which is conjugated to said mutant polypeptide,
wherein said conjugate retains angiogenic inhibitory activity, and wherein said conjugated entity is a monoclonal antibody, polyclonal antibody, or antigenic determinant which specifically interacts with said cells in need of treatment.

16. The method, according to claim 15, wherein said mutant polypeptide comprises the following amino acid sequence:

```
                                    10
        Glu Ala Glu Glu Asp Gly Asp Leu Gln Cys
                                    20
        Leu Cys Val Lys Thr Thr Ser Gln Val Arg
                                    30
        Pro Arg His Ile Thr Ser Leu Glu Val Ile
                                    40
        Lys Ala Gly Pro His Cys Pro Thr Ala Gln
                                    50
        Leu Ile Ala Thr Leu Lys Asn Gly Arg Lys
                                    60
        Ile Cys Leu Asp Leu Gln Ala Pro Leu Tyr
                                    70
     Gln Glu Ile Ile Gln Glu Leu Leu Glu Ser [COOH
``` or a fragment thereof which retains angiogenic inhibitory activity.

17. A substantially pure polypeptide conjugate free of other platelet proteins comprising
   (a) a mutant polypeptide of native PF4 selected from the group consisting of PF4-241, C-13-241, and C-41-241; and
   (b) an entity which is conjugated to said mutant polypeptide, wherein said conjugated entity is selected from the group consisting of monoclonal antibodies, polyclonal antibodies, fluorescein-isothiocyanate, fluorophores, toxins, cell receptor molecules, non-proteinaceous biological effector molecules, chelators, and carrier proteins.

18. The polypeptide conjugate, according to claim 1, wherein said mutant polypeptide comprises the following amino acid sequence:

```
                                    10
        Glu Ala Glu Glu Asp Gly Asp Leu Gln Cys
                                    20
        Leu Cys Val Lys Thr Thr Ser Gln Val Arg
                                    30
        Pro Arg His Ile Thr Ser Leu Glu Val Ile
                                    40
        Lys Ala Gly Pro His Cys Pro Thr Ala Gln
                                    50
        Leu Ile Ala Thr Leu Lys Asn Gly Arg Lys
                                    60
        Ile Cys Leu Asp Leu Gln Ala Pro Leu Tyr
                                    70
        Gln Glu Ile Ile Gln Glu Leu Leu Glu Ser
``` or a fragment thereof which retains angiogenic inhibitory activity.

* * * * *

UNITED STATES PATENT AND TRADEMARK OFFICE
CERTIFICATE OF CORRECTION

PATENT NO.     :   5,112,946

DATED          :   May 12, 1992

INVENTOR(S)    :   Theodore Maione

It is certified that error appears in the above-identified patent and that said Letters Patent is hereby corrected as shown below:

Column 13, claim 3    line 23: "entiry" should read --entity--.

Column 14, claim 16   line 29: "Gln Glu Ile Ile Gln Glu Leu Leu Glu Ser [COOH" should read --Gln Glu Ile Ile Gln Glu Leu Leu Glu Ser--.

Abstract (Title Page)   line 8: "modification of PF4" should read --modifications of PF4--.

Signed and Sealed this

Sixth Day of July, 1993

Attest:

MICHAEL K. KIRK

*Attesting Officer*     Acting Commissioner of Patents and Trademarks

UNITED STATES PATENT AND TRADEMARK OFFICE
CERTIFICATE OF CORRECTION

PATENT NO. : 5,112,946
DATED : May 12, 1992
INVENTOR(S) : Theodore Maione

It is certified that error appears in the above-indentified patent and that said Letters Patent is hereby corrected as shown below:

Column 11, line 24, "heparain" should read --heparin--.

Figure 10, Y-axis: Graduations of Y-axis "0 8 10 12 14 16" should read --6 8 10 12 14 16--.

Column 13, line 23, claim 3, "entiry" should read --entity--.

Column 14, line 29, claim 16, "Gln Glu Ile Ile Gln Glu Leu Leu Glu Ser [COOH" should read --Gln Glu Ile Ile Gln Glu Leu Leu Glu Ser--.

Abstract line 8: "modification of PF4" should read --modifications of PF4--.

Signed and Sealed this

Twenty-fourth Day of August, 1993

Attest:

BRUCE LEHMAN

*Attesting Officer*  *Commissioner of Patents and Trademarks*